United States Patent [19]

Welebir

[11] 4,411,685
[45] * Oct. 25, 1983

[54] 1-TRIACONTANOL PLANT GROWTH STIMULATOR FORMULATIONS

[75] Inventor: Andrew J. Welebir, Falls Church, Va.

[73] Assignee: Biochemical Research Corporation, Falls Church, Va.

[*] Notice: The portion of the term of this patent subsequent to Jun. 8, 1999, has been disclaimed.

[21] Appl. No.: 202,705

[22] Filed: Oct. 30, 1980

Related U.S. Application Data

[63] Continuation-in-part of Ser. No. 146,005, May 2, 1980, Pat. No. 4,333,758, which is a continuation-in-part of Ser. No. 47,696, Jun. 12, 1979, abandoned.

[51] Int. Cl.³ .................................................. A01N 59/00
[52] U.S. Cl. ........................................... 71/84; 71/82; 71/88; 71/114; 71/116; 71/65; 71/122
[58] Field of Search .................... 71/122, 114, 80, 84, 71/116, 117, 88, 95, 82

[56] References Cited

U.S. PATENT DOCUMENTS

| | | | |
|---|---|---|---|
| 2,229,948 | 1/1941 | Weil | 71/114 |
| 2,265,159 | 12/1941 | Grether | 71/114 |
| 4,150,970 | 4/1979 | Ries et al. | 71/122 |
| 4,169,716 | 10/1979 | Ashmead | 71/122 |
| 4,230,485 | 10/1980 | Ohlrogge | 71/122 |

FOREIGN PATENT DOCUMENTS 718073   3/1980   U.S.S.R. .................................. 71/122

OTHER PUBLICATIONS

Genkel et al., "Stimulative Effect, etc;" (1958) CA 55, No. 23686n (1961).

Primary Examiner—Glennon H. Hollrah
Attorney, Agent, or Firm—Birch, Stewart, Kolasch & Birch

[57] ABSTRACT

A plant growth stimulator formulation including a substantially water-soluble concentrate solution of 1-triacontanol, a polar organic solvent, metal ions, and other plant growth substances. Metal ions disclosed in the present invention markedly increase the growth-stimulating effect of 1-triacontanol when applied to plant life resulting in crop yield increases which may be as high as 50 to 100%. The addition of certain plant growth substances such as auxins, gibberellins, cytokinins and kinins, and brassins and brassinosteroids alter the plants' response to 1-triacontanol formulations containing metal ions, and broaden the range at which said metal ions are effective in assisting 1-triacontanol in stimulating plant growth.

20 Claims, 7 Drawing Figures

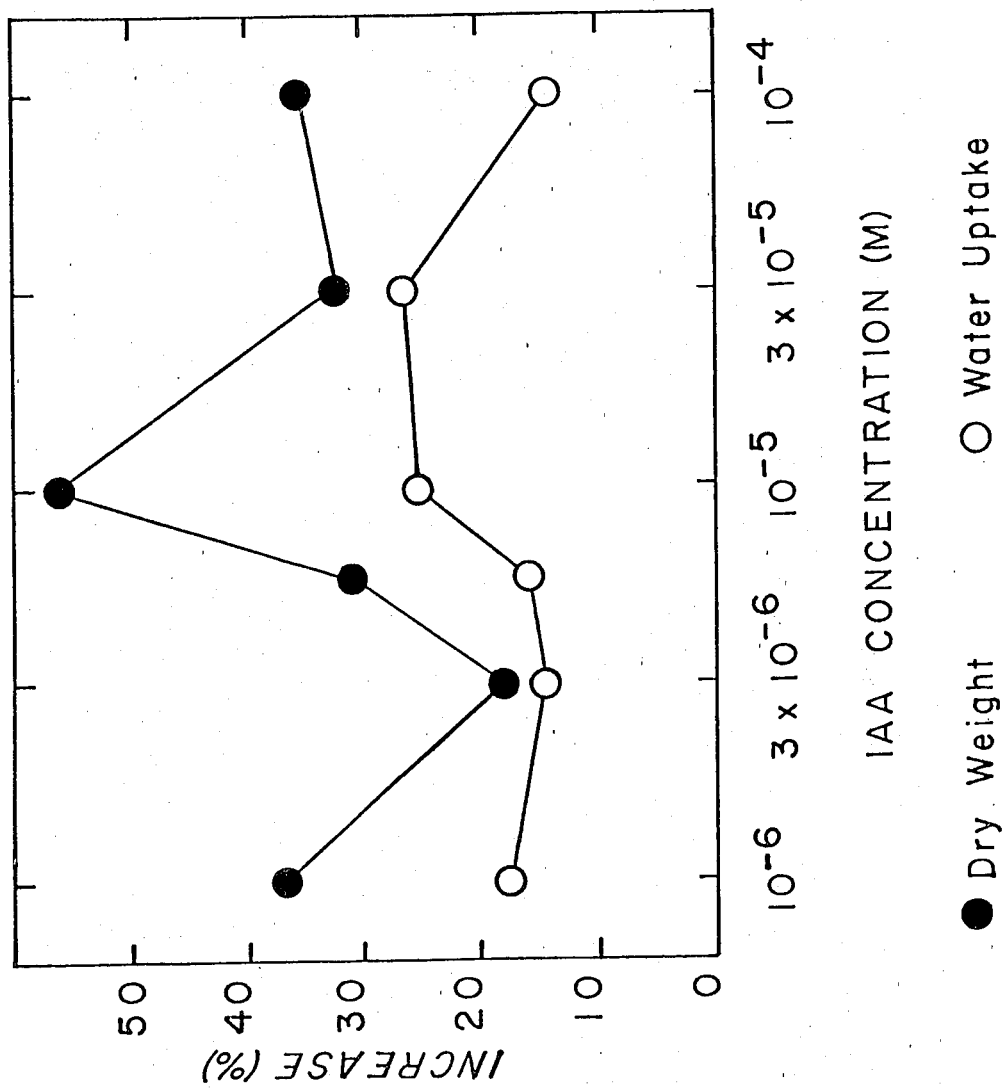

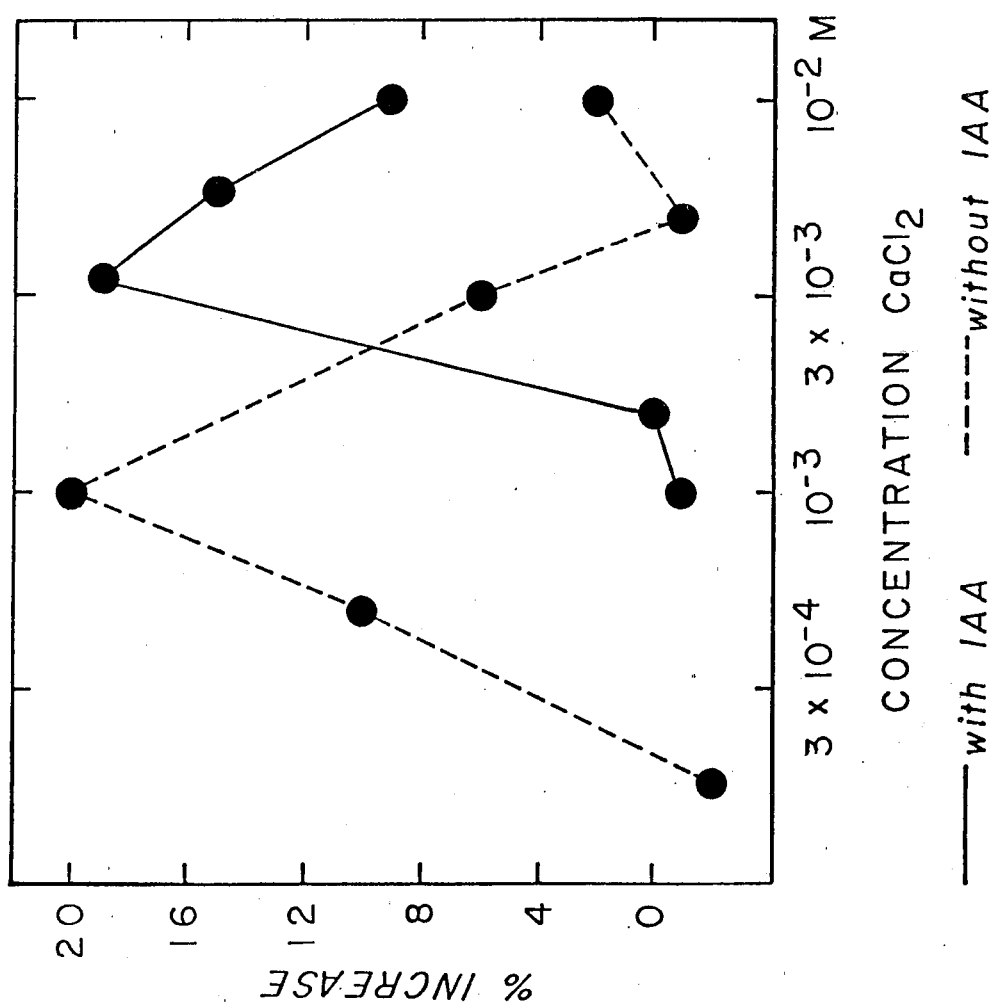

1-TRIACONTANOL PLANT GROWTH STIMULATOR FORMULATIONS

BACKGROUND OF THE INVENTION

This application is a continuation-in-part of copending U.S. application Ser. No. 146,005, filed May 2, 1980, now U.S. Pat. No. 4,333,758, which is a continuation-in-part of copending U.S. application Ser. No. 47,696, filed June 12, 1979 now abandoned.

Field of the Invention

The present invention relates to the chemical composition which, when applied to growing plants, is effective in stimulating plant growth. More particularly, the present invention is directed to a chemical formulation of 1-triacontanol in combination with a polar organic solvent, metal ions, other plant growth substances, and water.

Description of the Prior Art

Recently, 1-triacontanol, $CH_3(CH_2)_{28}CH_2OH$, has been under investigation as a naturally-occurring plant growth stimulant (see Ries, et al., Science, 195: 1339 (1977)). In fact, field trials are presently being conducted in an attempt to optimize the conditions at which a chemical formulation of this compound can be applied effectively to plants.

In the research that is presently being conducted utilizing 1-triacontanol as a plant growth stimulant, use is being made of a relatively large amount of surfactants in the chemical formulation in an attempt to render the 1-triacontanol soluble in water. Of course, the use of a large amount of water is imperative in order to economically and effectively apply the chemical formulation to large areas of growing plants. Accordingly, it is imperative to render the 1-triacontanol water-soluble so that it can be properly dispersed in a large quantity of water which is to be subsequently applied to plants. However, the organic solvents which are presently being utilized to make the 1-triacontanol soluble in water, for example, the use of certain chemicals such as chloroform and chemical surfactants and also the use of other water-insoluble solvents, have been found to be detrimental to both plant life and the environment. Thus, it has been found, for example, that the use of surfactants coats the plant, thereby preventing entry of the 1-triacontanol into the plant and, consequently, the plant growth-stimulating properties of the triacontanol are rendered less effective. Also, since it has been determined that the action of triacontanol appears to require calcium for optimum activity, the use of surfactants must be avoided to prevent complexation of the calcium ion.

It is known that calcium can alter the effects of plant hormones including indole-3-acetic acid (IAA). Other cations have also been found to affect plant growth and to affect the effects of plant growth regulators (see Poovaiah and Leopold, Plant Physiol., 58: 783 (1976)). The following cations have the ability to increase auxin binding to the cell membrane and inhibit IAA-stimulated growth in the order

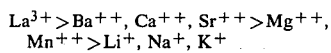

(Poovaiah and Leopold, Plant Physiol., 58: 182 (1976)).

IAA is known to rapidly stimulate cell elongation and enlargement, a process that involves loosening of the cell wall. IAA occurs primarily in esterified form, the myo-inositol ester comprising about fifty percent in *Zea mays*. Only about one to ten percent of the relatively large amount of IAA present compared to other plants occurs as free IAA. Auxin binding to cell membranes is a reversible process with a $K_m$ between $10^{-6}$ and $5 \times 10^{-5}$ M, and there are apparently two binding sites. Site 1 binds both active and inactive auxin analogs while site 2 appears to be auxin-specific.

The disclosure of H. H. Ashmead in U.S. Pat. No. 4,169,716 dated Oct. 2, 1979 teaches that 1-triacontanol may have a synergistic effect when incorporated into a formulation containing plant growth substances in the presence of metal proteinates. In accordance with the present invention, however, only metal ions and not metals complexed with proteins or surfactants are suitable. Furthermore, the prior art does not clearly show a synergistic effect with metal proteinates and triacontanol since triacontanol was not sprayed in solution without additives.

SUMMARY OF THE INVENTION

Accordingly, an object of the present invention is to provide an inexpensive and effective means of formulating 1-triacontanol without the use of surfactants of large quantities of organic solvents which have been found to adversely affect plant growth.

Another object of the present invention is to provide a chemical formulation which contains a polar organic solvent which renders 1-triacontanol soluble in water and at the same time poses no threat to plant life or the environment.

Pursuant to the present invention, the above problems have been eliminated by providing a chemical formulation which can be used with water for application to plant life. According to the present invention, 1-triacontanol is dissolved in a polar organic solvent in an amount sufficient to form a water-soluble concentrate. Typically, a concentrate can be formed by mixing together one part by weight (grams) of 1-triacontanol with up to about 5,000,000 parts by volume (ml) of the polar organic solvent, preferably between 1 and 500,000 ml of polar organic solvent to one gram of 1-triacontanol, more preferably one part by weight of 1-triacontanol to about 1000 parts by volume of the polar organic solvent and most preferably about one part of 1-triacontanol to about 40 to 140 parts of solvent. The polar organic solvent can be any water-soluble solvent or solvent mixture containing one or more functional groups which renders the 1-triacontanol solution soluble in water. This solution is then dissolved in a large quantity of water which contains metal salts and other plant growth substances with stirring and/or shaking. Alternately, other plant growth substances may be dissolved in the concentrate, the purpose of which will become clear in the following discussion.

The polar organic solvents which are utilized in the present invention to aid in the solubility of the 1-triacontanol in water include alcohols, ketones, water-soluble ethers, glycols, sulfoxides, and organic carboxylic acids and any other solvent or solvent mixture containing one or more functional groups contained in any one class or classes of said solvents. Typical polar organic solvents include acetone, methyl ethyl ketone, methanol, ethanol, isopropanol, n-butanol, diethylene glycol, propylene glycol, dioxane, acetic acid, and dimethyl sulfoxide (DMSO).

Typical ratios of the 1-triacontanol-organic solvent solution to water may vary from 1:10,000 to 1:1 parts by volume, preferably 1:1000 to 2:100 parts by volume, depending upon the desired concentration of the 1-triacontanol in the final solution.

In accordance with another aspect of the present invention, it has been discovered that indole-3-acetic acid, which normally stimulates plant growth, inhibits the plant growth-stimulating effects of 1-triacontanol in plants when the two are sprayed simultaneously as a binary mixture. Various plant growth substances were added to triacontanol formulations in order to improve the effectiveness of the plant growth-stimulating properties of the 1-triacontanol formulations. The following plant growth substances were tested: indole-3-acetic acid (IAA), gibberellic acid (GA$_3$), kinetin, 2,4-dichlorophenoxyacetic acid (2,4,-D), 2,3,5-triiodobenzoic acid (TIBA), and maleic hydrazide (MH). Various metal salts were also tested for their effectiveness in improving the plant growth-stimulating properties of the 1-triacontanol formulations. The salts tested included $CaCl_2$, $LaCl_3$, $Ce(SO_4)_2$, $MgCl_2$, $MnCl_2$, and mixtures thereof. it has been discovered that the presence of both 1-triacontanol and metal salts in the formulation creates a synergistic effect in increasing the plant growth-stimulating properties of the formulations. Although not wishing to be bound to any specific theory as to the precise mechanism by which the invention achieves its results, the plant growth-stimulating properties may be related to the fact that the metal ions ($Ca^{++}$, etc.) increase the binding of IAA to the cell membrane, and possible make it unavailable for binding to 1-triacontanol. Other possible mechanisms will become clear in the following discussion.

It has been found that the metal ions of the metal salts are most effective when applied to the leaves by spraying at concentrations of about $10^{-1}$ molar to $10^{-5}$ molar, preferably at concentrations of $10^{-2}$ molar to $10^{-4}$ molar and most preferably at concentrations of between $10^{-2}$ and $10^{-3}$ molar. Spraying should be done no earlier than about the fifth day (for corn) after germination or when the plant has 2 to 5 true leaves for best results. The metal ions should be sprayed on the area where the plants are grown in an amount of between $10^{-4}$ and $10^{-1}$ moles per acre, preferably in an amount of between $10^{-2}$ and $10^{-1}$ moles per acre using 10 liters/acre of the formulation or a proportional amount using higher volumes per acre.

Typically, the 1-triacontanol-polar organic solvent concentrate-water mixture is applied to the growing plants in an amount sufficient to achieve a distribution of at least 1 mg of 1-triacontanol per acre, advantageously, 5 to 20 mg per acre.

The chemical formulation, according to the present invention, can be applied to plant life in any desired manner although the spraying of the growing plant life has been found to be particularly effective when performed as described above.

The present invention can also be carried out by applying the metal salts or aqueous solutions of the metal salts to the to the soil where the seeds are planted and at a time up to several hours before the plants are treated with 1-triacontanol. For example, $10^{-1}$ to $10^{-3}$ molar aqueous solutions of $CaCl_2$ can be applied to the soil at a rate of about 200 ml per plant. It is preferable that each plant receive at least $10^{-4}$ moles of the metal ion. After several hours, in which time the plants have absorbed some of the metal ions, the plants can be sprayed with the 1-triacontanol solution or the 1-triacontanol can be added to the soil.

The metal salts which are useful are any salts or compounds which release metal ions in water. Inorganic salts are preferred. The size of the ionic radii of the metal ions appears to be related to the effectiveness of the ions in increasing crop yields. Metal ions which have ionic radii of about between 0.60 and 1.5 angstroms are useful, metal ions with radii of between 0.85 and 1.5 angstroms are preferred, and metals ions with radii between 0.95 and 1.3 angstroms are most preferred.

The average ionic radii of the preferred metal ions are listed below.

| Ion | Avg. radius (angstroms) | Ion | Avg. radius (angstroms) |
|---|---|---|---|
| $Ca^{++}$ | 1.08 | $Mn^{++}$ | 0.88 |
| $Sr^{++}$ | 1.24 | $La^{+3}$ | 1.10 |
| $Ba^{++}$ | 1.42 | $Ce^{+4}$ | 0.94 |
| $Cd^{++}$ | 1.05 | $Mg^{++}$ | 0.77 |
| $Pb^{++}$ | 1.19 | | |

The ionic radii of other metal ions which may be used in accordance with the present invention are listed below.

| Ion | Avg. radius (angstroms) | Ion | Avg. radius (angstroms) |
|---|---|---|---|
| $Ce^{+++}$ | 1.034 | $Pr^{+4}$ | 0.90 |
| $Cr^{++}$ | 0.89 | $Sm^{+3}$ | 0.964 |
| $Cu^{+2}$ | 0.96 | $Sm^{+2}$ | 0.93 |
| $Er^{+3}$ | 0.881 | $Tb^{+3}$ | 0.923 |
| $Eu^{+3}$ | 0.950 | $Tb^{+4}$ | 0.84 |
| $Eu^{+2}$ | 0.950 | $Ti^{++}$ | 0.94 |
| $Gd^{+3}$ | 0.938 | $Ti^{+3}$ | 0.95 |
| $In^{+3}$ | 0.81 | $Tm^{+3}$ | 0.87 |
| $Lu^{+3}$ | 0.93 | $V^{+2}$ | 0.88 |
| $Nd^{+3}$ | 0.995 | $Y^{+3}$ | 0.893 |
| $Pa^{+5}$ | 0.89 | $Yb^{+2}$ | 0.93 |
| $Pa^{+4}$ | 0.84 | $Yb^{+3}$ | 0.858 |
| $Pm^{+3}$ | 0.979 | | |
| $Pr^{+3}$ | 1.013 | | |

Metal ions which have a positive valence of at least +2 are most effective. Salts of the alkaline earth metals such as calcium ($Ca^{++}$), barium ($Ba^{++}$), and strontium ($Sr^{++}$) may be used with $Ca^{++}$ being preferred from this group because of its effectiveness, availability as a water-soluble salt, and its non-toxicity and exemption from tolerance by the U.S. Environmental Protection Agency (EPA). Other metals of Group II of the Periodic Table are also useful such as beryllium ($Be^{++}$) and magnesium ($Mg^{++}$). Metal ions from the lanthanide series are also very effective with metal ions from the lower end of the series such as lanthanum ($La^{+3}$) and cerium ($Ce^{+4}$) being preferred and lanthanum being most preferred from this series. Various metal ions from the transition metals are also useful. Of the transition metals, the lanthanide series metals are useful as discussed above as well as other transition metals such as manganese ($Mn^{++}$). Other useful metals include cadmium ($Cd^{+2}$), lead ($Pb^{+2}$), and iron salts, along with other similar metals as described above.

In summary, many different metal ions and mixtures thereof are useful in increasing plant growth when used in combination with triacontanol. The effectiveness of the metal ions is dependent upon the concentration at which they are used, the particular plant species to which they are applied, and various other factors, including pH, pH 7 or greater being preferred but not required for positive results. Therefore, it is possible that other metal ions than those discussed above might be useful in stimulating plant growth in accordance with the present invention.

The metal ions that appear to be most effective are $La^{+3}$, $Ca^{++}$, $Sr^{++}$, $Ba^{++}$, $Cd^{++}$, $Pb^{++}$, $Mn^{++}$, $Ce^{+4}$, and $Mg^{++}$, with $La^{+3}$ and $Ca^{++}$ showing the highest increase in crop yield and $Ca^{++}$ being most preferred because it is nontoxic and has been exempted from tolerance requirements by the EPA.

The chemical formulations of the present invention, without metal ions, when applied to field and sweet corn, sugar cane, tomatoes, cucumbers, beans and the like, have been found to increase growth in a greenhouse-controlled environment in an amount up to about 36% based upon the dry weight of the plants. Similar tests under field conditions on about 1,000 acres have resulted in an increase in crop yield of field corn of 6 to 16% measured in terms of bushels per acre.

The formulations of the present invention containing metal salts increased the dry weight yield of sweet corn up to 72% in a greenhouse-controlled environment as compared to up to 36% increases observed with formulations having no metal salts. The formulations having metal salts have also shown increases in the field ranging from 50 to 90% for beans, sweet corn, tomatoes, and cucumbers, and may be expected to increase the yield of crops such as radishes, soybeans, field corn, carrots, asparagus, sugar cane, and a variety of other crops. Other plants, such as those used for ornamental purposes, may be expected to respond equally well to the formulations with and without metal salts.

In accordance with another aspect of the present invention, the effects seen using the formulations containing various metal ions are also affected by other plant growth substances when they are incorporated into the solutions for application to plant life. Plant growth substances and growth-stimulating agents such as gibberellins, cytokinins, and auxins are especially effective. Examples of such substances are: gibberellic acid ($GA_3$, a gibberellin), kinetin and benzyladenine (cytokinins and kinins), indole-3-acetic acid and its salts and analogs (IAA, an auxin), other auxins such as indole-3-butyric acid (IBA), indole-3-acetonitrile, 2,4-dichlorophenoxyacetic acid (2,4-D), and brassins and brassinosteroids, such as brassinolide and its analogs.

It has been discovered that certain concentrations of metal ions in the formulations produce an optimum effect. Also, concentrations up to about 10-fold less than the optimum concentrations of the metal salts in the formulations containing 1-triacontanol produce significant increases in both dry weight and water uptake in plant life. Higher-than-optimum concentrations, however, tend to reverse the growth-stimulating effects of the 1-triacontanol formulations. While not wishing to be bound by the following mechanism whereby the invention may achieve its results, it may be hypothesized that the action of 1-triacontanol requires the presence of calcium or similar metal ions for its growth-stimulating action. Calcium, being basically a plant growth inhibitor at certain concentrations, is known to exert its inhibitory effect through the inhibition of endogenous auxin. The binding of auxins such as indole-3-acetic acid and naphthalene acetic acid is known to be promoted by the metal salts of the present invention, thereby causing the naturally occurring growth promoters to be unavailable for normal growth stimulation. Therefore, high concentrations of calcium or the other metal ions, concentrations above the optimum concentrations used in the formulations containing 1-triacontanol, appear to be detrimental to plant growth through the inhibition of auxin. Because of this, the increases observed in dry weight and water uptake in plant life are lowered above this optimum concentration of the metal salts even in the presence of 1-triacontanol.

It has been discovered during the course of research leading to the present invention that the inhibition of growth observed using high concentrations of metal ions is reversed when amounts of auxins and other plant growth-stimulating agents and hormones are added to the formulation. Therefore, in accordance with the present invention, other plant growth stimulating agents were added to the formulations of 1-triacontanol and metal ions.

It has further been discovered that, through the addition of other plant growth substances, much higher concentrations of metal ions than the optimum concentrations show favorable results. Increases in dry weight and water uptake were observed, for example, when the calcium concentration was raised from $10^{-2}$ molar to $5 \times 10^{-2}$ molar in the formulation of 1-triacontanol sprayed on sweet corn under a greenhouse-controlled environment. It was further found that the increases were comparable to those seen at the optimum calcium concentration of $10^{-2}$ molar, above which no increases in growth were observed without added auxin.

An advantage of this procedure is that costly determinations of calcium contained in the water used for spraying in order to obtain a formulation having the most effective $Ca^{++}$ concentration are effectively circumvented, since an excess of calcium or other metal ions may be used in the presence of the plant growth stimulants or hormones.

The preferred class of plant growth stimulants which show this effect when combined with 1-triacontanol and metal ions in solution for spraying plant life are auxins, examples of which are given above. While the plant growth stimulants may exert their effect at many concentrations, they are especially effective at concentrations between $10^{-6}$ molar and $10^{-4}$ molar, with concentrations between $6 \times 10^{-6}$ and $3 \times 10^{-5}$ being preferred. It is interesting to note that the preferred range of concentrations is the range of endogenous concentrations present in plant life.

The formulations of the present invention may include one or more metal ions in solution and, advantageously, one or more plant growth substances or stimulants in addition to an effective amount of 1-triacontanol. The formulations are effective in stimulating plant growth using all plants and crops and the conditions described previously. The plant growth substance added to the formulation may be dissolved previously in the concentrate containing 1-triacontanol and any of the polar organic solvents described herein, or may be dissolved in the water used to dissolve the concentrate prior to spraying. In addition to the plant growth stimulants used, their salts are likewise effective and show increased water solubility.

In addition to the above, higher concentrations of the metal ions may be added in the presence of the plant growth substances and 1-triacontanol. Concentrations of $10^{-5}$ molar to about 5 molar may be used, preferably concentrations of $10^{-4}$ to 1 molar, and most preferably concentrations of between $10^{-3}$ molar to $10^{-1}$ molar are effective.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 6 is a graph showing the relationship between the concentration of indole-3-acetic acid and the plant growth-stimulating effects of the formulation for sweet corn with a concentration of 1-triacontanol of 500 µg/l and concentration of $CaCl_2$ of $5 \times 10^{-2}$ molar; and FIG. 7 is a graph showing the relationship between the concentration of $CaCl_2$ and the plant growth-stimulating effects of the formulation for field corn with a concentration of 1-triacontanol of 500 µg/l, with and without the addition of indole-3-acetic acid ($10^{-5}$ M).

DETAILED DESCRIPTION

EXAMPLES

Figure 1:
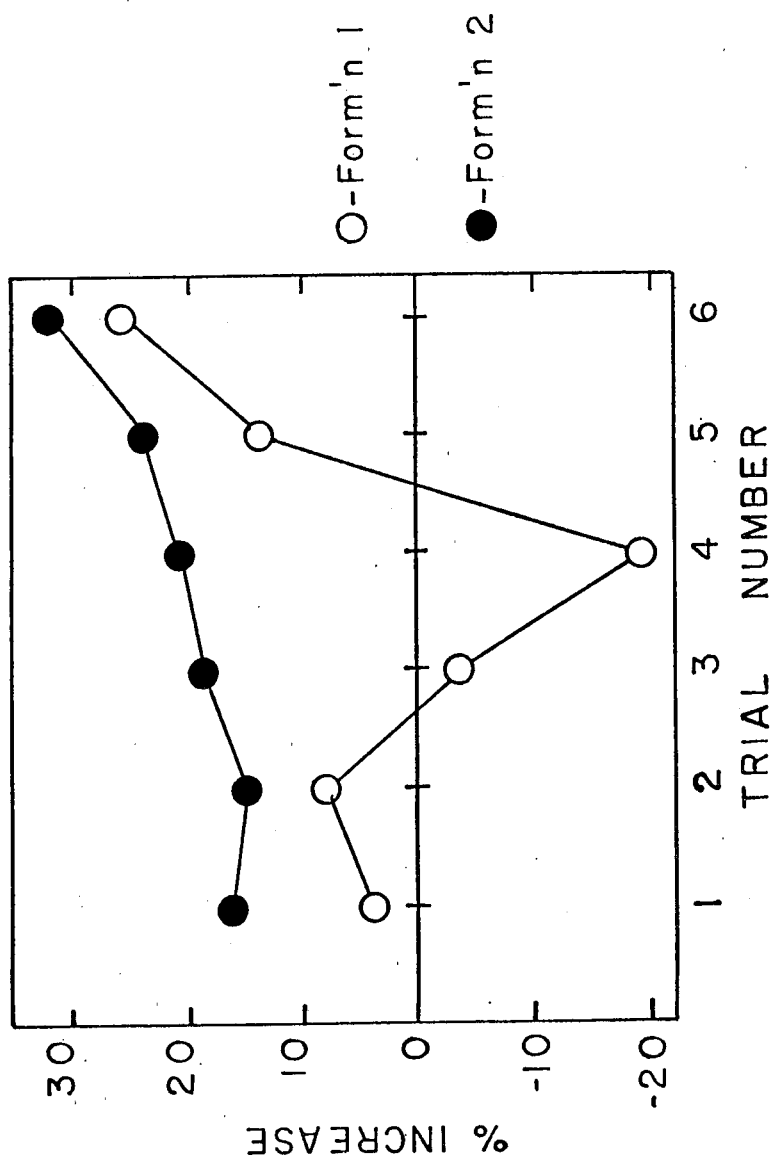
FIG. 1 is a graph showing the reproducibility in stimulating growth of sweet corn as determined by dry weight increases and the formulation used which contained 100 µg/l of 1-triacontanol without the addition of metal ions.

The following examples are presented herein as being exemplary of the present invention and, accordingly, should not be considered, in any way, as being limitative of the applicant's inventive contribution.

Example 1

A 1 mg quantity of 1-triacontanol was dissolved in 20 ml of boiling acetone (or methyl ethyl ketone) and the solution was cooled to room temperature. This was added to 980 ml of water with vigorous stirring over a 30-second period. The pH of the resultant solution was adjusted to pH 8 and may be applied to plant life aerially at a rate of 10 mg per acre using 10 liters of solution per acre. The solution may further be diluted with ten parts of water resulting in a rate of 1 mg per acre. Other dilutions or higher concentrations of 1-triacontanol may also be used.

Example 2

A 10 mg quantity of 1-triacontanol was dissolved in 100 ml of methanol (or 50 ml of ethanol) at the boiling point. The mixture was diluted to one liter with water at room temperature with vigorous stirring. The concentrate may be diluted resulting in a solution containing 1 mg of 1-triacontanol per liter. This solution may be applied as described under Example 1.

Example 3

One mg of 1-triacontanol was dissolved in 25 ml of hot isopropanol and the hot solution was poured into 975 ml of water with vigorous stirring over a one-minute period. This solution may be applied as described under Example 1.

Example 4

One mg of 1-triacontanol was dissolved in 25 ml of hot diethylene glycol and added to 975 ml of rapidly stirring water. The resulting solution may be used as described above.

Example 5

One mg of 1-triacontanol was dissolved in 10 ml of hot n-butanol and the mixture was added with stirring to 990 ml of water at 60 degrees. The solution was cooled to room temperature before use.

Example 6

Ten mg of 1-triacontanol was dissolved in 100 ml of warm dioxane and added over 60 seconds to 950 ml of warm water. The solution may be used as described under Example 1.

Example 7

One mg of 1-triacontanol was dissolved in 50 ml of hot propylene glycol and added to 950 ml of water with stirring. The solution may be used as described above.

Example 8

One mg of 1-triacontanol was dissolved in 20 ml of hot dimethyl sulfoxide (DMSO) and cooled to room temperature. The resultant solution was added to 980 ml of water with stirring prior to use. This solution may be used as described under Example 1.

Comparative Results

1-Triacontanol which had a melting point of 87° was prepared in accordance with the teachings of U.S. Pat. No. 4,167,641 entitled "Synthesis of Long-Chain Carboxylic Acids and Alcohols." All solvents were of reagent grade. Hybrid sweet corn seeds (var. Silver Queen) were obtained from Wetzel Seed Co., Harrisonburg, Va. Fertilizer (15-30-15) was purchased locally (Stern's "Miracle Grow"). Field corn seeds (Pfizer 95-day singlecross hybrid) were generously supplied by Pfizer Genetics, Olivia, Minn. and tomato seeds were the product of Ferry-Morse Seed Co., Inc., Fulton, Ky.

Indole-3-acetic acid, gibberellic acid (potassium salt), and kinetin were obtained from Calbiochem-Behring Corporation, La Jolla, Calif. 2,4-Dichlorophenoxyacetic acid, 2,3,5-triiodobenzoic acid, and maleic hydrazide were purchased from Aldrich Chemical Company, Milwaukee, Wisc. Inorganic salts were from Fisher Scientific Company and were of reagent grade.

For the purpose of the greenhouse experiments, seeds were planted 5 cm apart (1:1 vermiculite:peat, v/v) in trays 30×60×6 cm containing 30 to 40 plants each. Trays received one gram of 15-30-15 fertilizer after planting and received an average of 300 ml of water per day. On the seventh day (unless otherwise specified) after shoots appeared, plants were sprayed with the various formulations described below. Tomatoes were sprayed on day 36, and all plants were sprayed to the drip point. Eight-hour days and 16-hour nights were maintained (200 w/m$^2$ artificial light, unless otherwise specified) at temperatures of 20° C. and 25° C., respectively. The experiments done out-of-doors with seedlings varied with respect to watering and temperature with minimum temperatures between 8° C. and 18° C. and maximum temperatures between 25° C. and 35° C. for both the control plants and sprayed plants. Plants sprayed in field tests were treated with the described formulations when the plant had three to four true leaves.

All experiments with corn seedlings involved harvesting on day 14 and determining fresh weights. After drying the plants in an oven at 100° to 125° C. until constant weight was reached, the dry weights were subtracted from the fresh weights to give the water uptake increases.

A comparison study was made between the formulation of the Ries, et al., U.S. Pat. No. 4,150,970 and the surfactant-free formulation of the present invention. The following formulations were used in all experiments:

Formulation 1

A 100 μg quantity of 1-triacontanol was dissolved in 1 ml of chloroform and shaken prior to use with one liter of water containing 1 g of Tween 20 (Example II of the Ries, et al., U.S. Pat. No. 4,150,970).

Formulation 2

A 100 μg quantity of 1-triacontanol was dissolved in 20 ml of acetone at 50° C. and the resultant solution, which had an indefinite shelf life, was dissolved in 980 ml of water at room temperature.

Formulation 3

A 100 μg quantity of 1-triacontanol was dissolved in 50 ml of hot ethanol and the resultant solution was dissolved in 950 ml of water.

Formulation 4

A 100 μg quantity of 1-triacontanol was dissolved in 20 ml of acetone at 50° C. and the resultant solution was dissolved in an additional 20 ml of water to from a concentrate. Any additional plant growth substance to be added was then dissolved in the concentrate. The solution was diluted to one liter with water prior to use, with or without a specified amount of a metal salt.

Formulation 5

A 100 μg quantity of 1-triacontanol was dissolved in 20 ml of acetone at 50° C. and the resulting solution was dissolved in 980 ml of water containing a specified amount of a water-soluble plant growth substance, with or without the addition of a specified quantity of a metal salt.

Formulation 6

A 500 μg quantity of 1-triacontanol was dissolved in 20 ml of dioxane at 60° C. and the resultant solution was dissolved in 980 ml of water prior to use.

Formulation 7

A 500 μg quantity of 1-triacontanol was dissolved in 25 ml of propylene glycol at 90° C. and the solution was diluted to one liter for use.

Formulation 8

A 500 μg quantity of 1-triacontanol was dissolved in 20 ml of hot dimethyl sulfoxide (DMSO) and cooled to room temperature. The resulting solution was added to 980 ml of water prior to use.

Formulation 9

A 500 μg quantity of 1-triacontanol was dissolved in 20 ml of acetone at 50° C. and a specified quantity of a plant growth substance was added. The resultant solution was diluted to one liter in water containing a specified amount of a metal salt.

Formulation 10

A 500 μg quantity of 1-triacontanol was dissolved in 20 ml of acetone at 50° C. and the resulting solution was added to 980 ml of water containing a specified amount of metal salts with or without the addition of a specified amount of a water-soluble plant growth substance.

Formulation 11

A 100 μg quantity of 1-triacontanol was dissolved in 1 ml of chloroform and the solution was shaken with one liter of water containing one gram of Tween 20 and a specified amount of metal salts.

TABLE 1

Increases in Dry Weight and Water Uptake of 14-Day Old Hybrid Sweet Corn (var. Silver Queen) Sprayed with Various Formulations of 1-Triacontanol without the Addition of Metal Salts or Other Plant Growth Substances.

| FOR-MULA-TION | PERCENT INCREASES | | LEVEL OF SIGNIFICANCE | |
|---|---|---|---|---|
| | DRY WT. | H$_2$O UPTAKE | DRY WT. | H$_2$O UPTAKE |
| 1 | −19% | −8% | 0.005 | 0.05 |
| 1 | +10 | −10 | 0.07 | 0.07 |
| 2 | +21 | +16 | 0.005 | 0.005 |
| 2 | +19 | +29 | 0.06 | 0.02 |
| 2 | +36 | +19 | 0.01 | 0.08 |
| 3 | +19 | +6 | 0.06 | N.S. |
| 6 | +17 | +8 | 0.07 | N.S. |
| 7 | +33 | +20 | 0.002 | 0.03 |
| 8 | +18 | −9 | 0.02 | N.S. |

TABLE 2

Increases in Crop Yields Observed in the Field Spraying Two Different Formulations of 1-Triacontanol (1 mg/l) without the Addition of Metal Salts or Other Plant Growth Substances.

| CROP | FORMULATION | INCREASE PER ACRE |
|---|---|---|
| Hybrid Sweet Corn[a] | | |
| 'Silver Queen' | 1 | −24%[b] |
| | 2 | +21 |
| Beans | | |
| 'Blue Lakes Sringless'[c] | 1 | +29 |
| | 2 | +60 |

TABLE 2-continued

Increases in Crop Yields Observed in the Field Spraying Two Different Formulations of 1-Triacontanol (1 mg/l) without the Addition of Metal Salts or Other Plant Growth Substances.

| CROP | FORMULATION | INCREASE PER ACRE |
|---|---|---|
| Cucumbers | | |
| 'Straight Eight'[c] | 1 | −10 |
| | 2 | +39 |

[a]Increases were characterized by the increases in the fresh weight of marketable ears of corn.
[b]Results were significant at better than the 0.05 level.
[c]Increases characterized by a greater number of beans or cucumbers, which resulted in an increase in total fresh weight.

TABLE 3

Increases in Dry Weight and Water Uptake of 14-Day Old Hybrid Sweet Corn Seedlings (var. Silver Queen) Sprayed with a Variety of Plant Growth Substances with and without the Addition of 1-Triacontanol.

| PLANT GROWTH SUBSTANCE | CONCENTRATION (M) | TRIACONTANOL (100 µg/l) | FORMULATION | INCREASES[a] DRY WT. | $H_2O$ UPTAKE |
|---|---|---|---|---|---|
| IAA | $10^{-5}$ | NO | 4 | +4% | −7% |
| IAA | $10^{-5}$ | YES | 4 | +2 | −5% |
| $GA_3$ | $10^{-5}$ | NO | 5 | −24 | −6 |
| $GA_3$ | $10^{-5}$ | YES | 5 | −15 | −3 |
| Kinetin | $10^{-5}$ | NO | 4 | −24 | −3 |
| Kinetin | $10^{-5}$ | YES | 4 | −21 | +14 |
| 2,4-D | $10^{-5}$ | NO | 4 | +10 | −9 |
| 2,4-D | $10^{-5}$ | YES | 4 | +17 | −13 |
| TIBA | $10^{-4}$ | NO | 4 | +10 | −12 |
| TIBA | $10^{-4}$ | YES | 4 | +19 | +1 |
| MH | $10^{-4}$ | NO | 4 | +7 | −1 |
| MH | $10^{-4}$ | YES | 4 | +12 | −7 |
| — | — | YES | 2 | +20 | +16 |

[a]Least Significant Differences:
0.05 level, 7%;
0.01 level, 12%
Note:
The −7% increase observed for IAA sprayed alone was not significant.

TABLE 4

Increases in Dry Weight and Water Uptake of 14-Day Old Hybrid Sweet Corn Seedlings (var. Silver Queen) Sprayed with a Variety of Metal Salts and Formulations, with and without the Addition of 1-Triacontanol.

| METAL SALT | CONCENTRATION (M) | TRIACONTANOL (100 µg/l) | FORMULATION | INCREASES[a] DRY WT. | $H_2O$ UPTAKE |
|---|---|---|---|---|---|
| $CaCl_2$ | $10^{-2}$ | NO | 4 | +4% | −2% |
| $CaCl_2$ | $10^{-2}$ | YES | 4 | +65 | +11 |
| $CaCl_2$ | $5 \times 10^{-3}$ | YES | 4 | +50 | +21 |
| $CaCl_2$ | $10^{-3}$ | YES | 4 | +42 | +35 |
| $CaCl_2$ | $10^{-2}$ | YES | 11 | −5 | +9 |
| $CaCl_2$ | $5 \times 10^{-3}$ | YES | 11 | +5 | +6 |
| $LaCl_3$ | $10^{-2}$ | NO | 4 | +5 | −2 |
| $LaCl_3$ | $10^{-2}$ | YES | 4 | +72 | +18 |
| $Ce(SO_4)_2$ | $10^{-3}$ | YES | 4 | +21 | +26 |
| $MgCl_2$ | $10^{-3}$ | YES | 4 | +21 | +20 |
| $MnCl_2$ | $10^{-3}$ | YES | 4 | +9 | +29 |
| $MgCl_2 + CaCl_2$ | $10^{-3}$ ea. | YES | 4 | +39 | +30 |
| — | — | YES | 1 | +20 | +16 |

[a]Least Significant Differences:
0.05 level, 11%;
0.01 level, 20%

TABLE 5

Increases in Dry Weight and Water Uptake of 14-Day Old Field Corn Seedlings (var. Pfizer 95-Day Singlecross Hybrid) Sprayed with a Variety of Metal Salts and Formulations, with and without the Addition of 1-Triacontanol.

| METAL SALT | CONCENTRATION (M) | TRIACONTANOL (100 µg/l) | FORMULATION | INCREASES[a] DRY WT. | $H_2O$ UPTAKE |
|---|---|---|---|---|---|
| $CaCl_2$ | $10^{-3}$ | YES | 4 | +20-30% | +21% |
| $CaCl_2$ | $10^{-3}$ | YES | 11 | − 8 | −26 |
| $CaCl_2$ | $5 \times 10^{-4}$ | YES | 4 | +22 | + 8 |
| $CaCl_2$ | $10^{-3}$ | YES | 11 | −10 | −19 |
| $LaCl_3$ | $10^{-3}$ | YES | 4 | +25-32 | °25 |
| $CaCl_2 + MgCl_2$ | $10^{-3}$ ea. | YES | 4 | +20-30 | +6-18 |
| — | — | YES | 1 | − 3 | − 4 |

[a]Least Significant Differences:
0.05 level, 9%,
0.01 level, 14%

TABLE 6

Increases in Dry Weight and Water Uptake of 45-Day Old Tomatoes (var. Ponderosa Red Beefsteak) Sprayed on Day 36 with Calcium Chloride and 1-Triacontanol (100 µg/l) Using Different Formulations.

| CONCENTRATION OF $CaCl_2$ | FORMULATION | INCREASES DRY WEIGHT | $H_2O$ UPTAKE |
|---|---|---|---|
| $5 \times 10^{-3}$ M | 4 | +38% | +34% |
| $10^{-2}$ M | 4 | +43 | +10 |
| $10^{-3}$ M | 11 | − 1 | − 5 |
| $2.5 \times 10^{-3}$ M | 11 | + 2 | + 2 |
| — | 4 | − 3 | − 2 |
| — | 11 | + 6 | − 4 |

TABLE 7

Differences in Lengths between the Stems (to the First Internode, Length "a") and Total Plant Length (Length "b") over Controls of Hybrid Sweet Corn Seedlings (var. Silver Queen) Sprayed on Day 7 with a Variety of Plant Growth Substances, with and without 1-Triacontanol (T).

| PLANT GROWTH SUBSTANCE | LENGTH "a" | INCREASE | LENGTH "b" | INCREASE |
|---|---|---|---|---|
| IAA | 11.6 cm | 0% | 24.4 cm | −2% |
| IAA + T | 12.6 | +10 | 29.8 | +19 |
| GA$_3$ | 11.2 | −3 | 26.6 | −6 |
| GA$_3$ + T | 13.0 | +13 | 32.5 | +30 |
| Kinetin | 12.1 | +8 | 26.8 | +7 |
| Kinetin + T | 11.5 | 0 | 32.5 | +30 |
| Control$_1$ | 11.5 | 0 | 25.0 | 0 |
| T | 9.3 | +15 | 41.6 | +15 |
| CaCl$_2$ + T | 9.4 | +16 | 39.9 | +10 |
| Control$_2$ | 8.1 | 0 | 36.3 | 0 |

Note:
These data are presented to indicate changes in geometry of seedling growth when sprayed with various substances and do not reflect actual increases in tissue growth which would be indicated by increases in weight. Controls were sprayed with 2% acetone in water only.

TABLE 8

Results of Field Trials Spraying 1 mg/l of 1-Triacontanol (2% acetone) Containing Various Concentrations of Calcium Chloride at Alkaline pH.

| CROP | pH | CALCIUM CONCENTRATION (M) | INCREASE[a] |
|---|---|---|---|
| Tomatoes ('Ponderosa Red Beefsteak') | | | |
| Early | 7.8 | 5 × 10$^{-3}$ | 72% |
| Late | 7.8 | 5 × 10$^{-3}$ | 67 |
| Sweet Corn ('Silver Queen') | | | |
| Trial 1 | 8.2 | 10$^{-2}$ | 51 |
| Trial 2 | 8.2 | 10$^{-2}$ | 53 |
| Trial 3 | 8.2 | 10$^{-2}$ | 54 |
| Beans | | | |
| ('Blue Lakes Stringless') | 8.7 | 4.5 × 10$^{-3}$ | 90 |
| Cucumbers | | | |
| ('Straight Eight') | 8.7 | 4.5 × 10$^{-3}$ | 101 |

[a] Increase in fresh weight of marketable yield of crops over the marketable yield of the controls.

TABLE 9

Results of Spraying Second-Generation Hybrid Sweet Corn Seedlings (var. Silver Queen) with 1-Triacontanol (500 μg/l) in the presence of Calcium Chloride at a pH of 8.1 Using Acetone (2%) as the Polar Organic Solvent.

| GENERATION TEST SEED | GENERATION CONTROL SEED | CONCENTRATION CaCl$_2$ | INCREASES DRY WT. | INCREASES H$_2$O UPTAKE |
|---|---|---|---|---|
| SECOND (First was Sprayed Only) | SECOND (First and Second not Sprayed) | 1 × 10$^{-2}$ M | +44% | +40% |
| SECOND (First and Second Sprayed) | SECOND (First and Second not Sprayed) | 1 × 10$^{-2}$ (First) 1.1 × 10$^{-2}$ (Second) | +61 | +52 |
| SECOND (First and Second Sprayed) | SECOND (Second was Sprayed Only) | 1 × 10$^{-2}$ (First) 1.1 × 10$^{-2}$ (Second) | +22 | +9 |
| FIRST (Sprayed) | FIRST (Not Sprayed) | 1.1 × 10$^{-2}$ | +23 | −2 |

Note:
The lower increases observed spraying 1.1 × 10$^{-2}$ M CaCl$_2$ on the seedlings occurred since higher-than-optimum Ca$^{+2}$ was sprayed (see FIG. 3).

TABLE 10

Increases in Dry Weight and Water Uptake of Hybrid Sweet Corn Seedlings (var. Silver Queen) Sprayed with Formulations of 1-Triacontanol (500 μg/l, 2% Acetone) Containing Various Concentrations of CaCl$_2$ and Various Plant Growth Substances (pH 8).

| PLANT GROWTH SUBSTANCE | CONCENTRATION (M) | CONCENTRATION CaCl$_2$ (M) | INCREASES DRY WEIGHT | INCREASES H$_2$O UPTAKE |
|---|---|---|---|---|
| IAA | 1.0 × 10$^{-6}$ | 0.05 | +37% | +18% |
| IAA | 1.0 × 10$^{-5}$ | 0.05 | +56 | +25 |
| IAA | 1.0 × 10$^{-4}$ | 0.05 | +36 | +14 |
| GA$_3$ | 4.0 × 10$^{-5}$ | 0.01 | +16 | +15 |
| GA$_3$ | 4.0 × 10$^{-5}$ | 0.05 | +22 | +13 |
| Kinetin | 1.0 × 10$^{-5}$ | 0.01 | +3 | +13 |
| Kinetin | 1.0 × 10$^{-5}$ | 0.05 | +1 | −2 |

TABLE 11

Increases in Dry Weight and Water Uptake of Field Corn Seedlings (Pfizer 95-Day Singlecross Hybrid) Sprayed with a Brassinosteroid[a] with and without a Formulation of 1-Triacontanol (500 μg/l, 2% Acetone) Containing 0.01 M CaCl$_2$.

| FORMULATION | DRY WEIGHT INCREASE | WATER UPTAKE INCREASE |
|---|---|---|
| Brassinosteroid (4 × 10$^{-7}$ M) without 1-Triacontanol | +11% | +8% |
| Brassinosteroid (4 × 10$^{-7}$ M) with 1-Triacontanol | +19 | +10 |

[a] The compound used, 2α, 3α, 22α, 23α-tetrahydroxy-24α-methyl-B—homo-5α-cholestan-6-one, a brassinolide analog, was dissolved in the acetone concentrate containing 1-triacontanol according to formulation 9.

Figure 2:
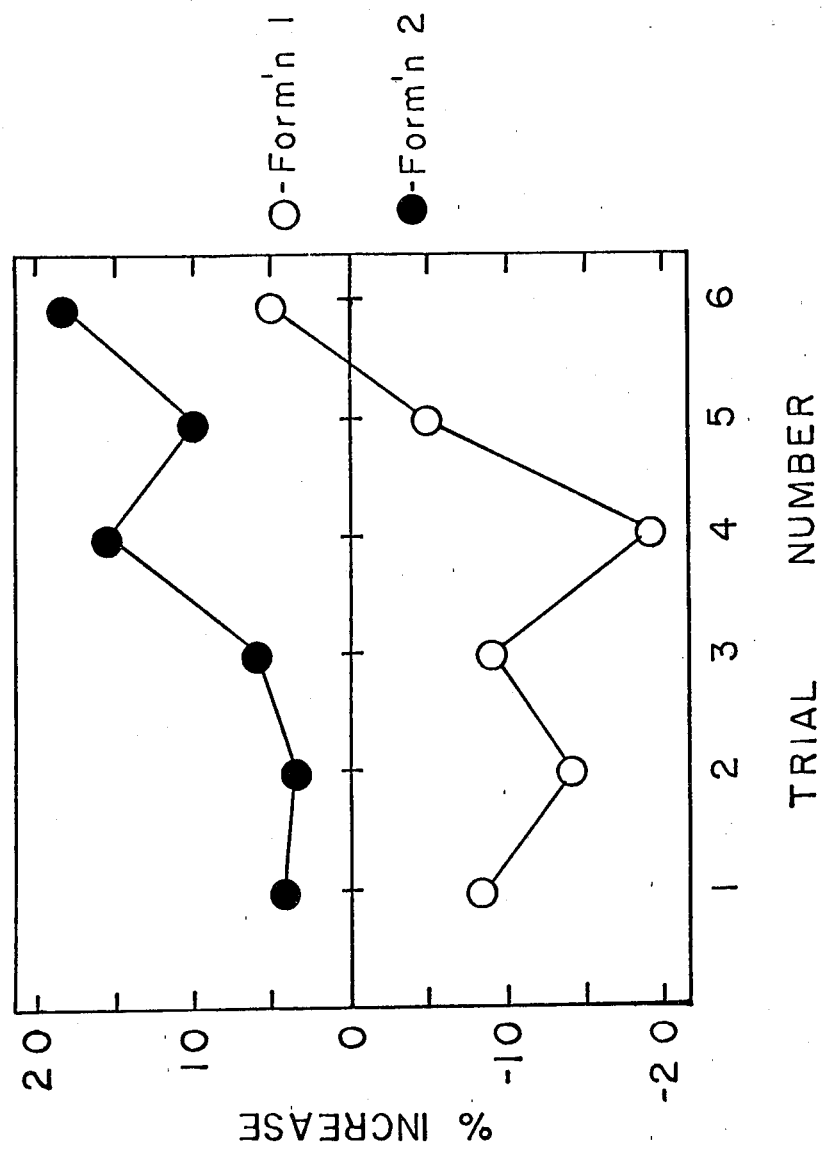
FIG. 2 is a graph showing the reproducibility in stimulating growth of sweet corn as determined by water uptake increases and the formulation used which contained 100 µg/l of 1-triacontanol without the addition of metal ions.

As shown in Table 1, the formulations of 1-triacontanol, containing 1-triacontanol and polar organic solvents in water only, significantly increased the dry weight and water uptake of sweet corn seedlings while the formulation of U.S. Pat. No. 4,150,970 gave inconsistent results (see FIGS. 1 and 2). The dry weight increases were seen to correlate with the fresh weight (marketable yield) of crops when sprayed in the field.

Table 3 shows that no improvement in the formulations containing polar organic solvents, triacontanol, and water were found when other plant growth substances were added to the formulation without metal ions. However, when metal ions of the present invention were added to the formulation, significant increases in dry weight and water uptake were observed over those found using the formulations without metal ions (Tables 4, 5, and 6). The addition of surfactant additives to aid in the solubilization of nonpolar solvents, such as those used in U.S. patent application Ser. No. 4,150,970, was found to negate this effect and cause decreases in dry weight and water uptake. Since the present invention teaches that metal ions may be necessary for the growth-stimulating action of 1-triacontanol, complexing the ions would result in little or no growth stimulation.

U.S. Pat. No. 4,169,716 discloses formulations containing 1-triacontanol, plant growth substances, and polyvalent metals complexed to proteins, the combination of which shows increases in plant weight when applied to seedlings. The significant increases disclosed therein, however, are observed only when metal proteinates are applied without the addition of plant growth substances or 1-triacontanol, since the percent increase observed when triacontanol was added to the metal proteinates or when triacontanol was added to a mixture of metal proteinates and one or more plant growth substances was only about 1 to 4%.

Table 7 shows the change in the geometry of plants at harvest when sprayed with various formulations of the present invention. These data should not be interpreted as indicating increases in actual tissue growth. The dry weight increases found with the seedlings, a parameter indicating actual growth increases, are shown to correlate with those increases in marketable yield found in the field when the formulations containing metal ions and 1-triacontanol were sprayed (Table 8).

Figure 3:
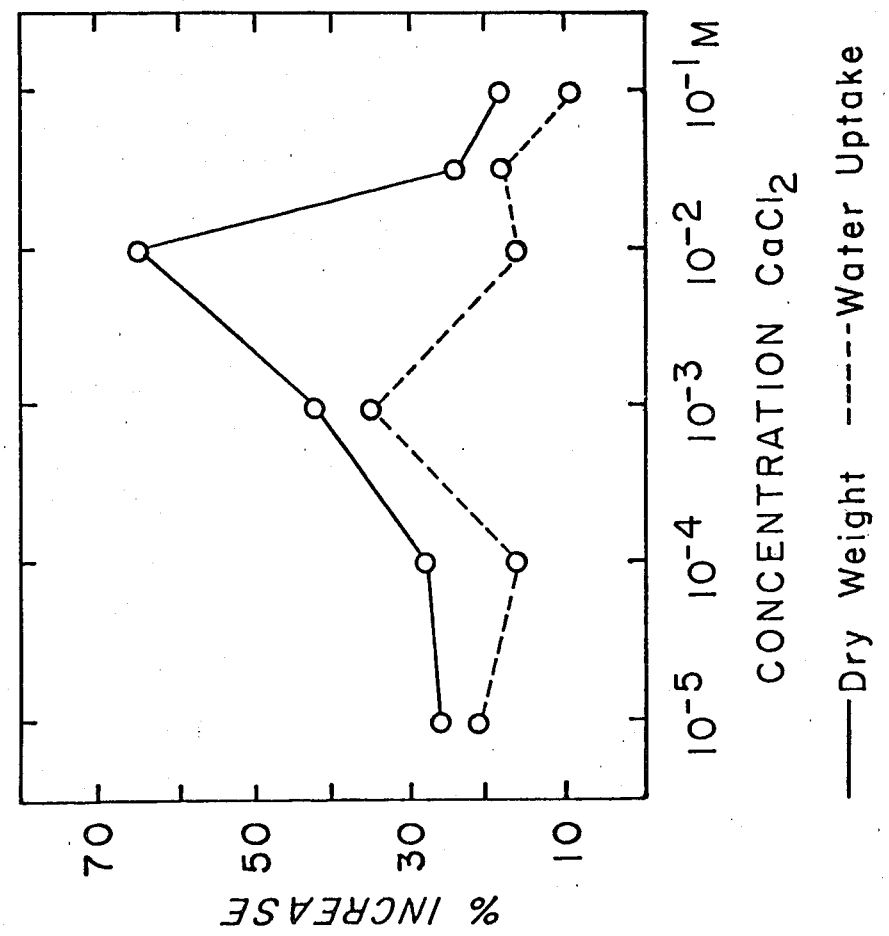
FIG. 3 is a graph showing the relationship between the concentration of $CaCl_2$ and the increase in the plant growth-stimulating effects of the formulation for sweet corn with a concentration of 1-triacontanol of 100 µg/l.
Figure 4:
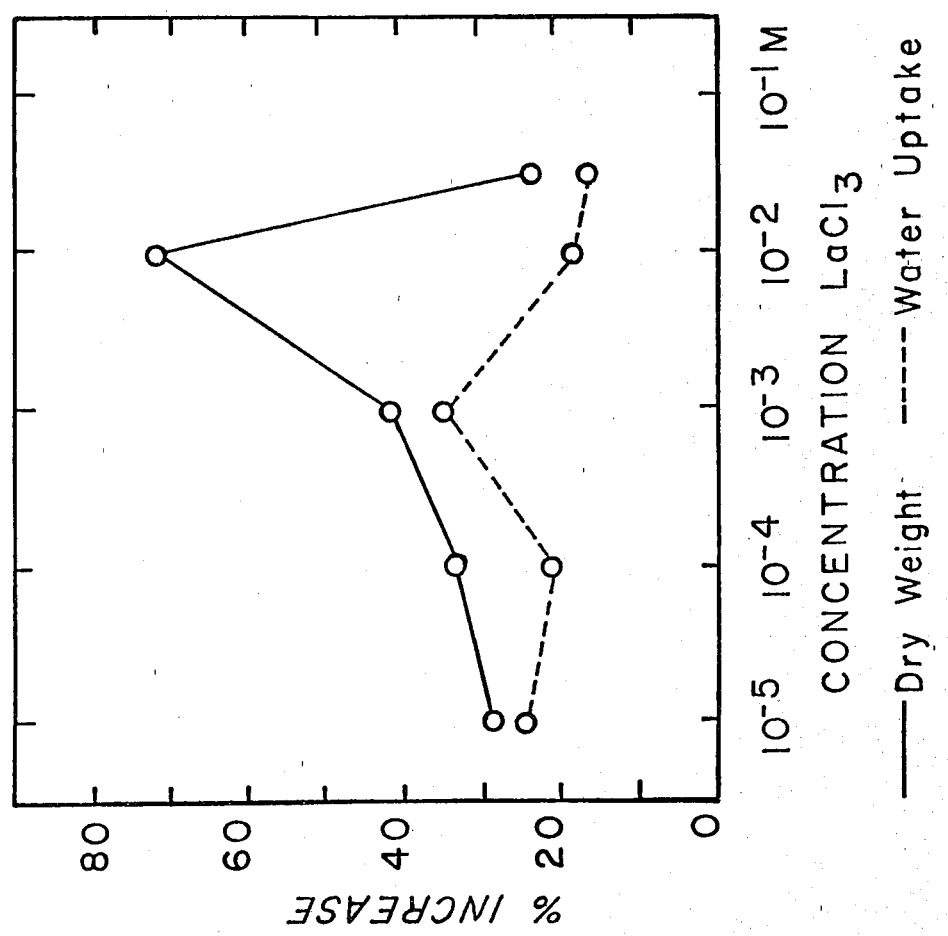
FIG. 4 is a graph showing the relationship between the concentration of $LaCl_3$ and the increase in the plant growth-stimulating effects of the formulation for sweet corn with a concentration of 1-triacontanol of 100 µg/l.
Figure 5:
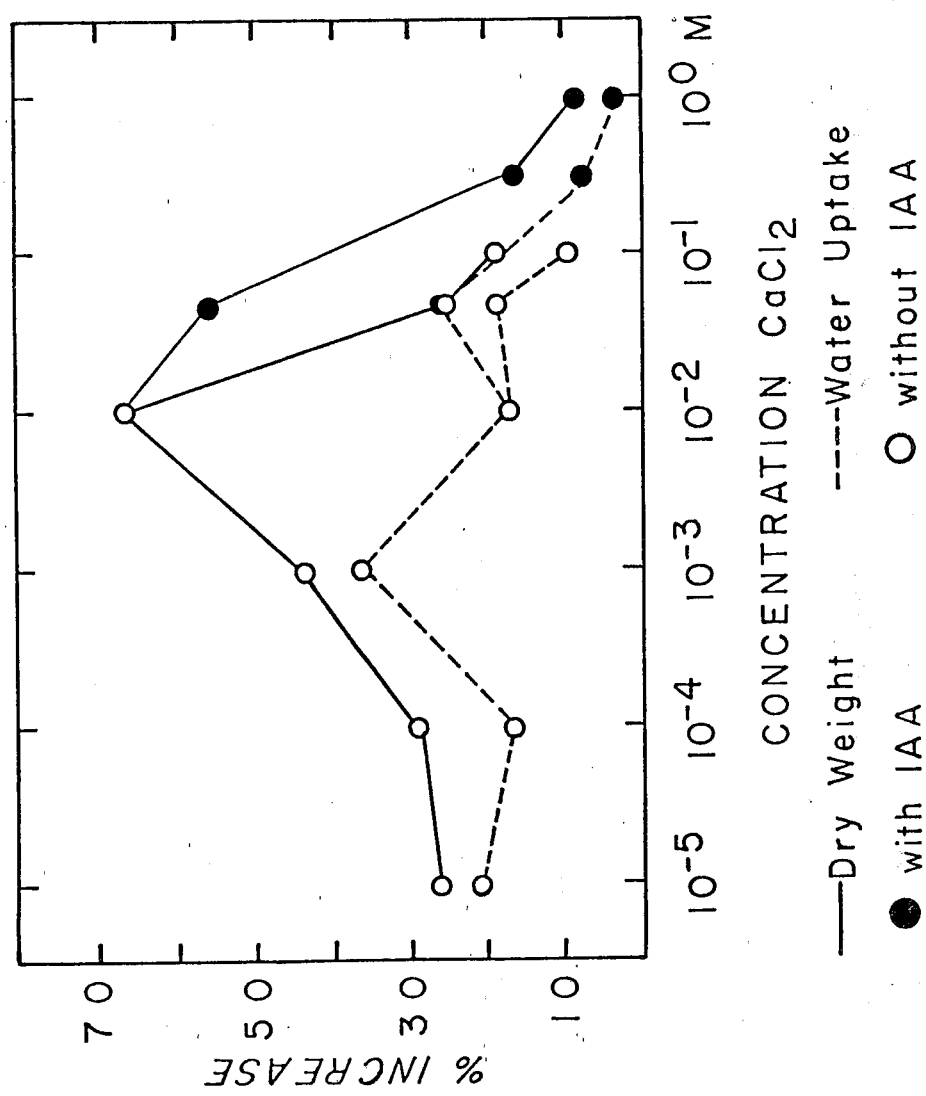
FIG. 5 is a graph showing the relationship between the concentration of $CaCl_2$ and the plant growth-stimulating effects of the formulation for sweet corn with a concentration of 1-triacontanol of 500 µg/l, with and without the addition of indole-3-acetic acid ($10^{-5}$ M)

When the metal ion concentration exceeds its optimum, a reversal of the plant-growth stimulating effect becomes apparent as shown in FIGS. 3 and 4. This effect was altered or reversed by the addition of plant growth substances described in the present invention (see FIG. 5 and Tables 10 and 11). Indole-3-acetic acid is seen to reach an optimum effect at $10^{-5}$ M, approximately the endogenous IAA concentration, when the concentration of $CaCl_2$ was raised to five times its optimum level. FIG. 6 shows the effect of IAA when combined with a formulation containing 1-triacontanol and 0.05 M $CaCl_2$ (five times the optimum concentration). The concentration range for the metal ion is shown to be wider when IAA is added, and the $Ca^{+2}$ concentration is no longer critical since a range of concentrations all produce an optimum effect.

This observation becomes important when considering the case for field corn (FIG. 7). Field corn seedlings show increases in dry weight and water uptake at a very narrow range which is optimum at only $10^{-3}$ M $CaCl_2$. Since the $Ca^{+2}$ concentration of hard water used to economically formulate 1-triacontanol for spraying in the field varies to a high degree, and may be in excess of $10^{-3}$ M in some cases, analysis of the water used must be undertaken in order to provide a formulation which will assure positive results when sprayed on crop seedlings. Since this adds considerable expense to the operation, the addition of IAA (or another plant growth substance that allows for increases in dry weight when triacontanol is sprayed with higher-than-optimum concentrations of metal ions) is desirable. The addition of IAA at $10^{-5}$ M gives a formulation that allows for significant increases in dry weight even at ten times the optimum level of $CaCl_2$, i.e., $10^{-2}$ M. At elevated levels of $Ca^{+2}$, the $Ca^{+2}$ present in hard water becomes negligible, since optimum results are seen not only at concentrations about $3 \times 10^{-3}$ M, but a concentrations twice that. Therefore, the use of the formulations of the present invention that contain 1-triacontanol, metal ions, and plant growth substances does not require the added expense of water analysis to successfully increase crop yields of field corn.

Table 9 shows that the effect of spraying the 1-triacontanol formulations of the present invention does not cause subsequent generations of the same plant to become unaffected by triacontanol spraying. Also, the second generation (the plants grown from the seed of sprayed plants) give increases in yield without being sprayed with triacontanol. Spraying these seedlings gives an additional increase equal to the increase found when the first generation seedlings are sprayed. This effect may be due to the fact that ears of sweet corn from triacontanol-sprayed plants contain the same number of kernels as those ears which were not sprayed, however, the kernels are larger in size. Planting the larger seed produces larger seedlings.

From these examples it is clear that metal ions significantly increase the growth-stimulating effect of 1-triacontanol, and also that auxins and other plant growth substances significantly increase the tolerance of the plant toward large concentrations of the metal ions.

The invention being thus described, it will be obvious that the same way be varied in many ways. Such variations are not to be regarded as a departure from the spirit and scope of the invention, and all such modifications as would be obvious to one skilled in the art are intended to be included within the scope of the following claims.

What is claimed is:

1. A plant growth stimulator formulation, consisting essentially of an effective plant growth-stimulating amount of 1-triacontanol; a water-soluble polar organic solvent in which 1-triacontanol is soluble; metal ions having a valence of +2 through +5, inclusive; an auxin; and water, said metal ions and said auxin being present in an amount effective to assist the 1-triacontanol in stimulating plant growth.

2. A plant growth stimulator formulation according to claim 1, wherein said metal ions are selected from the group consisting of $Ca^{+2}$, $La^{+3}$, $Sr^{+2}$, $Ba^{+2}$, $Cd^{+2}$, $Pb^{+2}$, $Zn^{+2}$, $Mn^{+2}$, $Mg^{+2}$ and $Ce^{+4}$.

3. A plant growth stimulator formulation according to claim 2, wherein said metal ion is $Ca^{+2}$.

4. A plant growth stimulator formulation according to claim 2, wherein said metal ion is $La^{+3}$.

5. A plant growth stimulator formulation according to claim 2, wherein said metal ions are present at a concentration between about $10^{-1}$ Molar and $10^{-5}$ Molar.

6. A plant growth stimulator formulation according to claim 2, wherein said metal ions are present at a concentration between about $10^{-2}$ Molar and $10^{-4}$ Molar.

7. A plant growth stimulator formulation according to claim 1, wherein said auxin is selected from the group consisting of indole-3-acetic acid, naphthalene acetic acid, 2,4-dichlorophenoxyacetic acid, and 2,4,5-trichlorophenoxyacetic acid.

8. A plant growth stimulator formulation according to claim 7, wherein said auxin is naphthalene acetic acid.

9. A plant growth stimulator formulation according to claim 1, wherein said auxin is present at a concentration of between about $10^{-6}$ Molar and $10^{-4}$ Molar.

10. A plant growth stimulator formulation according to claim 1, wherein said auxin is present at a concentration of between about $6 \times 10^{-6}$ Molar and $3 \times 10^{-5}$ Molar.

11. A plant growth stimulator formulation according to claim 8, wherein the naphthalene acetic acid is present at a concentration of about $10^{-6}$ Molar.

12. A formulation according to claim 1, wherein said polar organic solvent is selected from the group consisting of alcohols, ketones, water-soluble ethers, glycols, and organic carboxylic acids.

13. A formulation according to claim 1, wherein said polar organic solvent is selected from the group consisting of acetone, methyl ethyl ketone, methanol, ethanol, isopropanol, diethylene glycol, n-butanol, dioxane and acetic acid.

14. A formulation according to claim 1, wherein said polar organic solvent is a ketone.

15. A formulation according to claim 1, wherein said polar organic solvent is acetone.

16. A formulation according to claim 1, wherein said metal ions are dissolved in said formulation as metal salts.

17. A formulation according to claim 16, wherein said metal salt is $CaCl_2$.

18. A method for stimulating the growth of plants, comprising the steps of: spraying an effective plant growth-stimulating amount of the composition of claim 1 onto the leaves of growing plants.

19. A method according to claim 18, wherein the spraying is done when the plant has between 2 and 5 true leaves.

20. A method for stimulating the growth of plants which comprises spraying an effective plant growth stimulating amount of the formulation according to claim 1, 2, 3, 4, 5, 7, 8, 9 or 17, onto the leaves of corn, cucumber, bean or tomato plants.

* * * * *